United States Patent [19]

Lewis et al.

[11] Patent Number: 4,461,913

[45] Date of Patent: Jul. 24, 1984

[54] PRODUCTION OF UREA PHOSPHATE

[75] Inventors: Harry T. Lewis; Ewell F. Dillard, both of Florence, Ala.

[73] Assignee: Tennessee Valley Authority, Muscle Shoals, Ala.

[21] Appl. No.: 376,809

[22] Filed: May 10, 1982

Related U.S. Application Data

[63] Continuation of Ser. No. 324,515, Nov. 24, 1981, now Defensive Publication No. T. 103,206.

[51] Int. Cl.$^3$ .............. C07C 126/08; C07C 127/01; C07F 15/04
[52] U.S. Cl. ............................. 564/063; 260/439 R; 564/73
[58] Field of Search ............... 564/63, 73; 260/439 R

[56]  References Cited

U.S. PATENT DOCUMENTS

| | | | |
|---|---|---|---|
| 1,951,518 | 3/1934 | Meiser et al. | 564/73 X |
| 3,058,810 | 10/1962 | Huxley et al. | 564/73 X |
| 3,180,735 | 4/1965 | Titus | 564/73 X |
| 4,169,882 | 10/1979 | Sheridan | 564/73 X |
| 4,217,128 | 8/1980 | Stinson et al. | 564/73 X |

OTHER PUBLICATIONS

New Routes, "Chemical and Engineering News", p. 22, Sep. 1, 1975.
Kume, "Petroleum Refiner", vol. 39, No. 5, pp. 200–201, (1960).

*Primary Examiner*—Robert V. Hines
*Attorney, Agent, or Firm*—Robert A. Petrusek

[57]  ABSTRACT

A two-stage continuous crystallization process for production of urea phosphate by reaction of impure wet-process orthophosphoric acid (about 54 percent $P_2O_5$) and urea with simultaneous addition of a selected acidifying agent (sulfuric acid, hydrochloric acid, or phosphoric acid) to clarified mother liquor used as recycle in the process. Addition of the acidifying agent decreases pH in the crystallization process whereby the solubility of a contaminating water-insoluble iron phosphate-urea salt [$FeH_3(PO_4)_2 \cdot 2CO(NH_2)_2$] is increased, purity of the crystalline urea phosphate product is improved significantly, and the useful storage life of the recycle mother liquor is prolonged.

8 Claims, 4 Drawing Figures

PRODUCTION OF UREA PHOSPHATE FROM UREA AND MERCHANT-GRADE WET-PROCESS PHOSPHORIC ACID

APPARATUS USED IN BENCH-SCALE PRODUCTION OF UREA PHOSPHATE

BENCH-SCALE ADDITION OF UREA MELT TO FIRST STAGE

RELATIONSHIP OF PRODUCT PURITY VS. pH IN PROCESS

PRODUCTION OF UREA PHOSPHATE

The invention herein described may be manufactured and used by or for the Government for governmental purposes without the payment to us of any royalty therefor.

This application is a continuation of application Ser. No. 324,515 filed Nov. 24, 1981 for PRODUCTION OF UREA PHOSPHATE and now Defensive Publication T103,206.

INTRODUCTION

Our invention relates to an improvement in method for production of urea phosphate. It relates, more particularly, to a two-stage continuous crystallization process for the production of urea phosphate by the reaction of impure merchant-grade wet-process orthophosphoric acid (about 54 percent $P_2O_5$) with urea; and more particularly to the addition of acidifying agents to decrease pH in the aforementioned crystallization process whereby the solubility of a contaminating precipitate in the recycle mother liquor is increased and the purity of the urea phosphate product is significantly improved. This contaminating phase has been identified and characterized by us and is a new compound consisting of an iron phosphate-urea salt to which we have assigned the formula $FeH_3(PO_4)_2 \cdot 2CO(NH_2)_2$. Still more particularly our invention relates to the aforementioned crystallization process in which the addition of acidifying agents prolong the useful storage life of the recycle mother liquor.

BACKGROUND OF THE INVENTION

1. Field of the Invention

Urea phosphate [$CO(NH_2)_2 \cdot H_3PO_4$] is a dry, white crystalline material that melts at 243.5° F. It contains 17.7 percent nitrogen and 19.6 percent phosphorus which is equivalent to 44.9 percent $P_2O_5$. Urea phosphate is acidic (pH of 1 percent solution, 1.8), very soluble in water, and has a specific gravity of 1.759. The critical humidity of the material is 75 percent to 80 percent at 86° F. and is similar to urea. It is well known that urea phosphate is a finished fertilizer. Agronomic tests of the material have shown that it is an efficient source of nitrogen and phosphate for plant growth. Numerous investigators of the prior art have proposed the use of urea phosphate as an intermediate in the production of solid and liquid fertilizers containing polyphosphate.

Wet-process orthophosphoric acid is prepared by the acidulation of phosphate rock (mainly fluoroapatite) with sulfuric acid and separating the resulting calcium sulfate from the acidulate. The wet-process acid contains impurities from the phosphate rock such as iron, aluminum, magnesium, fluorine and calcium. In addition, unless the phosphate rock is calcined before it is acidulated, the acid contains dissolved and suspended carbonaceous matter which imparts a black, opaque color to the acid. It is difficult to make high quality liquids from wet-process acid containing all of its impurities. Methods for separating impurities from wet-process acid have been described by numerous investigators. Most of these methods are solvent extraction processes. Use of solvent extraction techniques require large quantities of expensive solvents which must be recovered. Also, the solvents only partially eliminate metallic impurities and sulfate from the acids. In the urea phosphate crystallization process, most of the impurities are separated from the phosphoric acid by reacting the acid with urea and crystallizing the adduct, urea phosphate, from the solution; most of the impurities from the acid remain in the mother liquor. The reaction of urea and phosphoric acid to form urea phosphate is shown by the following equation:

$$CO(NH_2)_2 + H_3PO_4 \rightarrow CO(NH_2)_2 \cdot H_3PO_4$$

The urea phosphate is then crystallized from the solution. The urea-phosphoric acid reaction and the crystallization of urea phosphate are both exothermic. The enthalpy of producing crystalline urea phosphate from equimolar amounts of urea and phosphoric acid (75 percent $H_3PO_4$) at 77° F. is −44 calories per gram. To produce solutions containing polyphosphate, the solid urea phosphate first is heated, either by external means or by chemical heat of ammoniation, to form urea-ammonium polyphosphate melt. This melt then is used to produce relatively pure solution fertilizers. Procedures similar to those involved in this process have been reported in the literature.

Description of the Prior Art

Heretofore, the reaction of phosphoric acid with urea has been studied by a number of investigators, beginning, we believe, with the work described in a German Patent (No. 286,491) granted to Badische Anilin and Soda-Fabrik in 1914. In this work, one mole of urea was reacted with one mole of phosphoric acid (50 percent). The solution was cooled to crystallize urea phosphate and the crystals were separated from the mother liquor. The patent claims the use of urea phosphate as a fertilizer. Clarkson and Braham (U.S. Pat. No. 1,440,056) added one mole of urea/mole $H_3PO_4$ to a solution containing 55-75 percent $H_3PO_4$ and separated the resulting crystals of urea phosphate from the solution. According to the disclosure, evaporation of water from urea-phosphate solutions should be carried out at low temperatures since decomposition becomes rapid above 194° F.

Somewhat more recently, Keens (British Pat. No. 1,149,924) proposed production of urea phosphate continuously in a vacuum crystallization process. The process utilized unconcentrated phosphoric acid and urea solution as feed material and involved heating and evaporation of the solution to yield a supersaturated solution of urea phosphate which was contacted with a suspension of growing urea phosphate crystals in mother liquor. The mother liquor was recycled to the feed solution. The final product crystals consisted of larger crystals which were more suitable for the manufacture of fertilizers. Mansfield (German Offen. Pat. No. 2,322,114) prepared urea phosphate by passing 90 percent $H_3PO_4$ at 95° F. and 90 percent urea at 239° F. into a tube of 6 m length and 5° inclination with countercurrent passage of warmed air. By this method, urea phosphate of <0.7 percent moisture content at ~95° F. was obtained. Greidinger and Cytter (German Offen. No. 2,429,030) describe a process for the manufacture of urea phosphate, useful as a fertilizer, by reaction of urea with anhydrous $H_3PO_4$ optionally with the addition of Mg, CO, Fe, Zn, Cu or Mn trace elements.

In still another patent, Koebner, Edwards and Williams (British No. 1,191,635) prepared urea phosphate as an intermediate from wet-process $H_3PO_4$ and treated the urea phosphate with an alkali metal or ammonium hydroxide or carbonate to produce orthophosphate and regenerate urea. The orthophosphate is separated as product and the urea is recycled. The reaction is preferably carried out in recycled mother liquor.

Methods of utilization of Vrea phosphate as the starting material for production of ammonium polyphosphate-type fertilizers have been proposed. These processes involve thermal decomposition of urea phosphate and utilize the condensing action of urea in urea phosphate to form polyphosphates. Among those is one method described by Theobald (German Patent No. 2,308,408) who proposes a two-stage process where urea phosphate is melted in the first stage and pyrolyzed into polyphosphate in the second stage.

In U.S. Pat. No. 3,713,802, Gittenait utilizes urea phosphate as the starting material for producing liquid and solid urea-ammonium polyphosphate. In the production of urea phosphate, unpurified wet-process phosphoric acid containing 30–60 percent $P_2O_5$ is reacted directly with urea (solid or solution). Mother liquor is added to increase fluidity. The urea phosphate is crystallized out after one hour, for example, and removed from the mother liquor by centrifuging. Most of the mineral impurities accompanying the wet-process acid remain in the mother liquor. Stinson, Mann, and McCullough (U.S. Pat. No. 4,217,128) describe a process for production of urea-ammonium polyphosphates by pyrolysis of crystalline urea phosphate in one stage. Molten urea-ammonium polyphosphates that contain up to 95 percent of the phosphate as polyphosphate are obtained. These are then processed into high-analysis solid or liquid fertilizers. Addition of urea to the process to maintain a urea:biuret ratio of at least 16 prevents precipitation of biuret in the liquid fertilizers.

Kozo Fukuba (Japanese Pat. No. 49-8498) describes a method of production of a highly purified, water-insoluble ammonium polyphosphate. The process involves calcination of dried urea phosphate, under an ammonia atmosphere, at 390° F. to 570° F.

In the production of the intermediate urea phosphate by Fukuba, wet-process acid (29 percent $P_2O_5$, as per example, produced by decomposition of Morrocan rock with sulfuric acid) was treated batchwise with caustic soda or sodium carbonate to remove some of the fluorine and silica; a large proportion of the organic materials in the acid are removed by using activated carbon and the acid is then concentrated to 45 to 55 percent by weight $P_2O_5$ content. Urea is reacted with the concentrated wet-process acid and recycle mother liquor is added for fluidity. The mole ratio of urea to $H_3PO_4$ in the feed is 0.9 to 1.5. The reaction to yield urea phosphate is carried out at about 120° 1 F. to 160° F. The reaction mixture is cooled to about 40°0 F. to 86° F. and crystalline urea phosphate is separated from the mother liquor. Fukuba's patent is characterized by the production of ammonium polyphosphate and the recycling of the mother liquor in the urea phosphate production system. Also, Fukuba discloses that addition of sulfuric acid increases yield of urea phosphate produced by the reaction of wet-process acid and urea.

SUMMARY OF THE INVENTION

Our invention is directed toward an improvement in processes for the production of urea phosphate. It, unlike the prior art referred to supra, involves the addition of acidifying agents such as phosphoric acid, sulfuric acid or hydrochloric acid in a two-stage continuous crystallization process for production of urea phosphate by the reaction of impure wet-process acid (about 54 percent $P_2O_5$) with urea whereby: (1) pH in the crystallization process is decreased, (2) the solubility of the contaminating water-insoluble iron phosphate-urea salt, which normally precipitates in the mother liquor, is increased, (3) the purity of the crystalline urea phosphate product is improved significantly, and (4) the useful storage life of the recycle mother liquor is prolonged. In essence, these improvements, referred to supra, constitute the novelty of our invention.

We have found that in our two-stage continuous crystallization process for the production of urea phosphate from impure merchant-grade wet-process acid and urea, a buildup of impurities occurs in the mother liquor used as recycle in the process. Recycle mother liquor is added to decrease suspension density and increase fluidity of the urea phosphate in each stage. Mother liquor also aids in separation in the centrifuge of product crystals from fine solid impurities containing iron, aluminum, magnesium, fluorine, and other impurities originally present in the feed wet-process acid. The product crystals in our continuous crystallization process contain only about 10 to 15 of these objectionable impurities and about 80 percent of the acid $P_2O_5$ and urea. The remainder of the phosphate and urea, and essentially all of the water and particulate carbonaceous material leave the process as byproduct mother liquor. The impurity level in the recycle mother liquor increases until steady state conditions are reached. In our production work with impure merchant-grade acids, Florida black acid derived from uncalcined phosphate rock and North Carolina green acid from calcined phosphate rock as examples, we found that at near steady state conditions the impurity level (impurity: $P_2O_5$ ratio) of the recycle mother liquor was about 3.5 times greater than in the feed wet-process acid; the $Fe_2O_3$ content in the recycle mother liquor was in the range of 1.5 to 2.0 percent. We have discovered through our experiments that fine-grained crystals of the compound $FeH_3(PO_4)_2.2CO(NH_2)_2$ precipitate when the iron content of the recycle mother liquor increases to approximately 0.7 percent iron (1.00 percent $Fe_2O_3$). Thus, it is readily apparent that in a continuous crystallization process precipitation of the iron phosphate-urea contaminant will occur in the recycle mother liquor before steady state conditions are reached. The presence of this contaminating compound is objectionable and limits the effectiveness of the process. Petrographic analysis indicates that it is present on the surface of the urea phosphate product crystals and is trapped between the crystals in the centrifuging step of the process to separate mother liquor from the urea phosphate crystals. The presence of the iron phosphate-urea salt leads to "blinding" in the centrifuge causing retention of an excessive amount of mother liquor and fine particulate carbonaceous material which results in decrease in product purity and loss of production time used to wash out these impurities from the screen or filter media in the centrifuge.

OBJECTS OF THE INVENTION

It is therefore an object of the present invention to produce urea phosphate in a two-stage continuous crystallization process by the reaction of impure merchant-grade wet-process acid with urea and simultaneous addition of an acidifying agent ($H_2SO_4$, $H_3PO_4$, or HCl) to the recycle mother liquor wherein: (1) pH in the process [pH in the urea phosphate slurry in the second stage (crystallizer)] is decreased; (2) solubility of the contaminating iron phosphate-urea salt [$FeH_3(PO_4)_2$.-

2CO(NH$_2$)$_2$] is increased and its precipitation essentially eliminated; and (3) the average purification level of the urea phosphate product (reduction of impurity level calculated by comparing aluminum to P$_2$O$_5$, iron to P$_2$O$_5$, magnesium to P$_2$O$_5$, and fluorine to P$_2$O$_5$ ratios of the product with those of the feed acid) is increased.

A further object of the present invention is to prolong the storage life of urea-ammonium polyphosphate liquid fertilizers obtained by pyrolysis of urea phosphate followed by addition of water and ammonia gas.

A still further object of the present invention is to prolong the useful storage life of the recycle mother liquor and thus increase the effectiveness of the process.

Another object of the present invention and advantage of adding an acidifying agent (H$_2$SO$_4$, for example) is that extra heat would be generated for evaporation of water during ammoniation of the byproduct mother liquor for conversion to a solid or granulated fertilizer product.

Still another advantage of the present invention of adding sulfuric acid in the process is that the solid or suspension fertilizer made from the byproduct mother liquor will contain sufficient sulfur for supplying the needs of sulfur deficient soils which exist in about 60 percent of the farmland in the United States.

Still further and more general objects and advantages of the present invention will appear from the more detailed description set forth below, it being understood, however, that this more detailed description is given by way of illustration and explanation only and not necessarily by way of limitation since various changes therein may be made by those skilled in the art without departing from the true spirit and scope of the present invention.

DESCRIPTION OF THE DRAWINGS

Our invention, together with further objects and advantages thereof will be better understood from a consideration of the following description taken in connection with the accompanying drawings in which.

Figure 1:
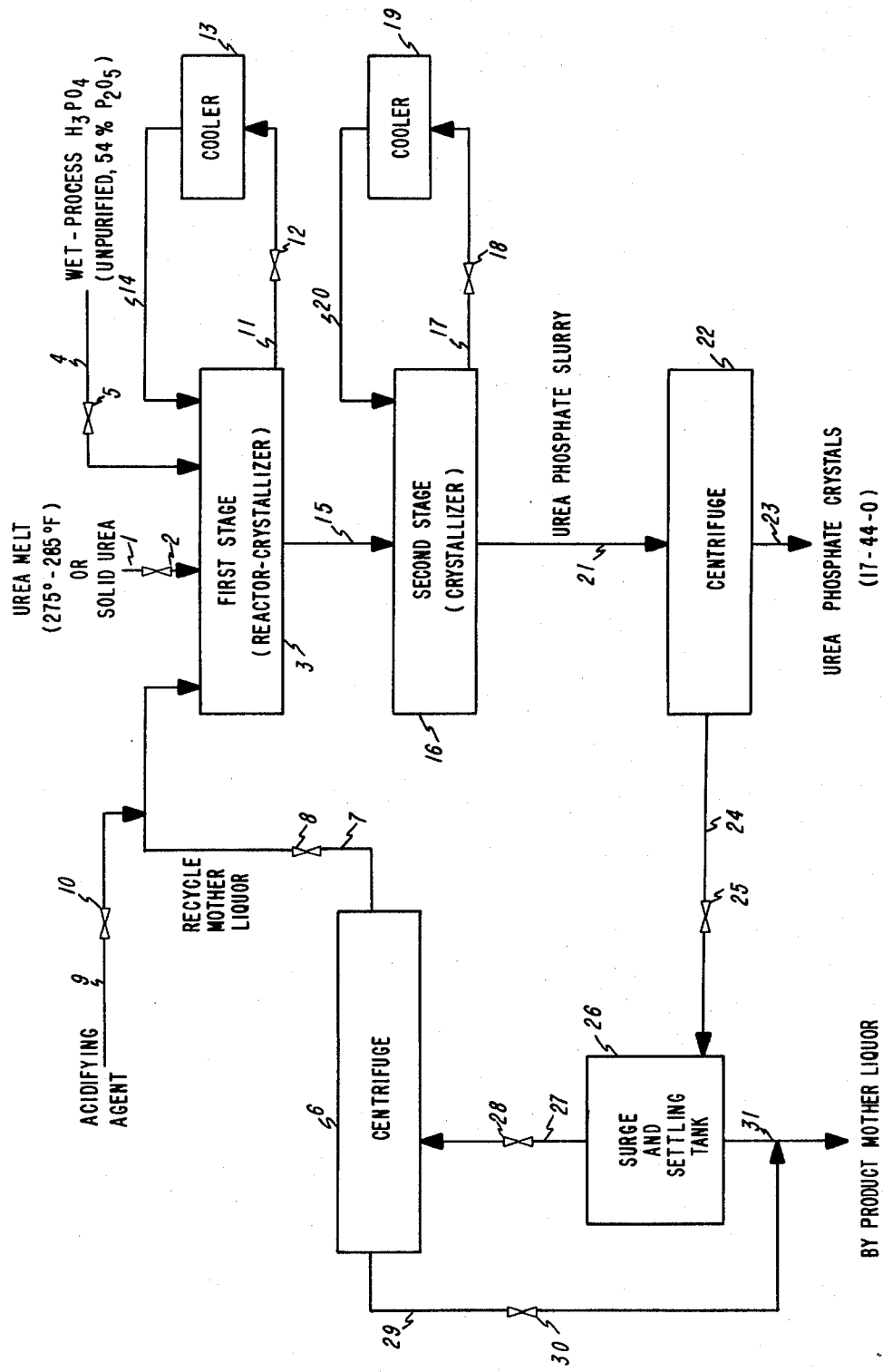
FIG. 1 is a flowsheet illustrating the principles utilized in carrying out our invention for the production of urea phosphate.
Figure 2:
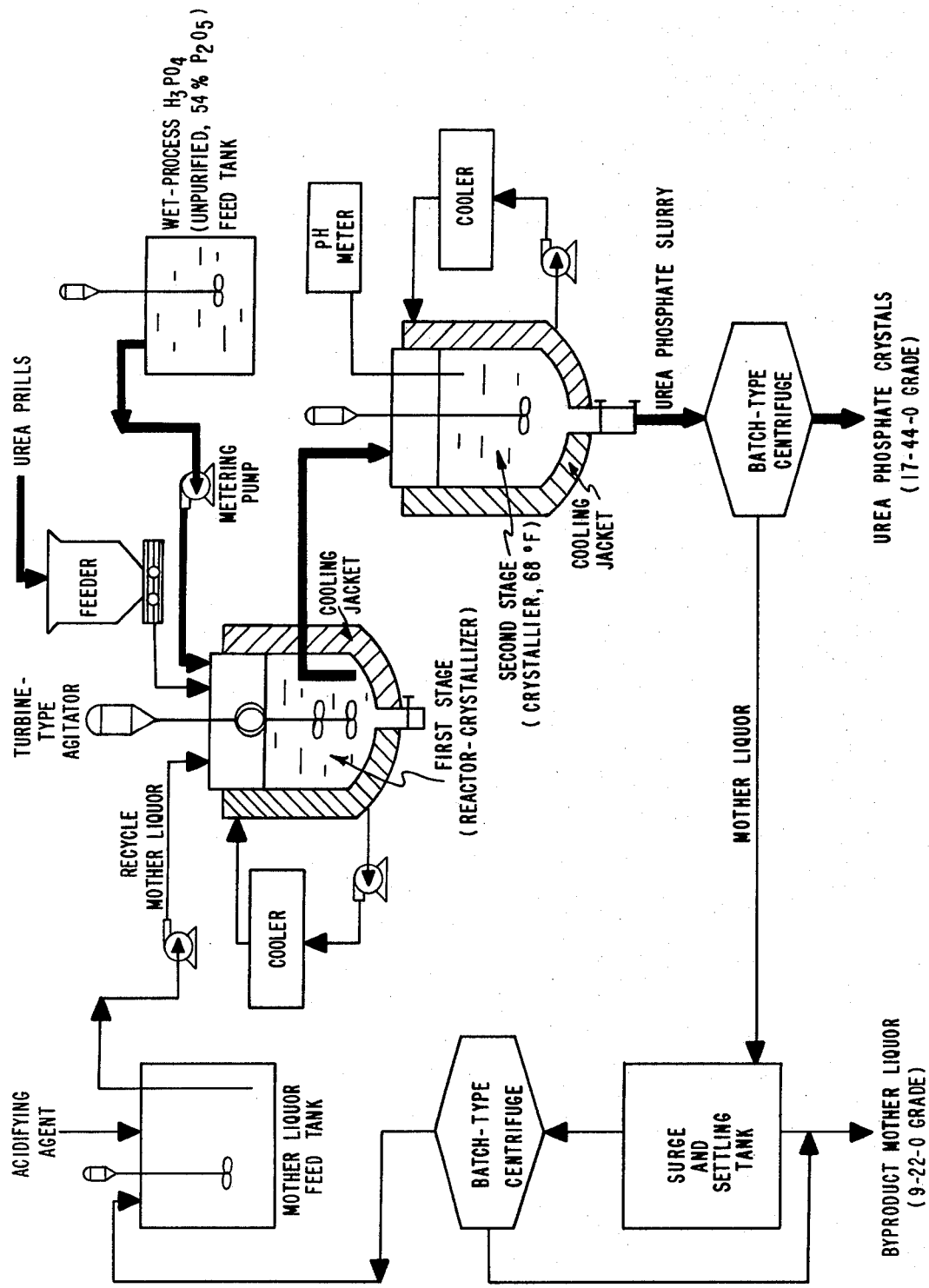
FIG. 2 is a diagram of the equipment we used in carrying out tests of our invention on a smaller scale than that of a commercial plant and of a size generally referred to as bench-scale.

Referring now more specifically to FIG. 1, urea melt (275°–285° F.) from the concentrator of a urea production plant (not shown) or solid urea, source also not shown, is fed via line 1 and means for control of feed rate 2 to first-stage reactor-crystallizer 3. Merchant-grade wet-process orthophosphoric acid (54 percent P$_2$O$_5$) from a source not shown is fed to first stage 3 via line 4 and means of control 5. Simultaneously, clarified recycle mother liquor is mixed with an acidifying agent (H$_2$SO$_4$, H$_3$PO$_4$, or HCl) and fed to first stage 3. The clarified recycle mother liquor is fed to first stage 3 from centrifuge 6 via line 7 and means of control 8. The acidifying agent is fed from a source not shown via line 9 and means of control 10 to line 7 where it is introduced with the recycle mother liquor to first stage 3. The acidifying agent may be fed at a rate to maintain a predetermined percent by weight of the agent in the recycle mother liquor to give the desired pH in the second stage of the process. First-stage reactor-crystallizer 3 is cooled below saturation temperature of the solution; thus some crystallization occurs therein. The temperature of first-stage reactor-crystallizer 3 is controlled by any suitable means such as is shown in FIG. 2. Referring again to FIG. 1, cooling is illustrated by circulating the reaction mixture in first-stage reactor-crystallizer 3 via line 11 and means of control 12 through cooler 13 with return to first-stage reactor-crystallizer 3 via line 14. Urea phosphate slurry from first-stage reactor-crystallizer 3 overflows to second-stage crystallizer 16 via line 15. Crystallization is completed in second-stage crystallizer 16 where the urea phosphate slurry is further cooled to the desired temperature (for example 68° F., which gives a high recovery of urea phosphate and is close to ambient temperature) by circulation via line 17 and means of control 18 through cooler 19 with return via line 20 to second-stage crystallizer 16. The two stages that are used for the process give better control of crystallizing conditions and growth of larger crystals. Also, when urea melt is used, two stages are necessary to prevent excessive nucleation caused by the large temperature difference between the melt (275°–285° F.) and the desired crystallizing temperature in the second stage (for example, 68° F.). For a urea phosphate product of high purity relatively large crystals are necessary. The weight ratio of recycle mother liquor to feed acid and retention time requirements depend upon the degree of product purity desired and increase as the impurity content of the feed acid increases. Urea phosphate slurry is withdrawn from second-stage crystallizer 16 via line 21 and product crystals are separated from mother liquor in centrifuge 22. The product crystals, 17-44-0 in grade, are discharged from centrifuge 22 to a storage area not shown via line 23. Mother liquor from centrifuge 22 is discharged via line 24 and means of control 25 to surge and settling tank 26. Part of the mother liquor is used as recycle to first-stage reactor-crystallizer 3 after settling in surge tank 26 and discharge via line 27 and means of control 28 to centrifuge 6 where essentially all solid impurities are removed. The remainder of the mother liquor containing the major portion of the impurities that were originally present in the wet-process acid leaves the process as byproduct mother liquor via line 29 and means of control 30 and via line 31. The byproduct liquor is suitable for processing into suspension or granular fertilizers.

Figure 3:
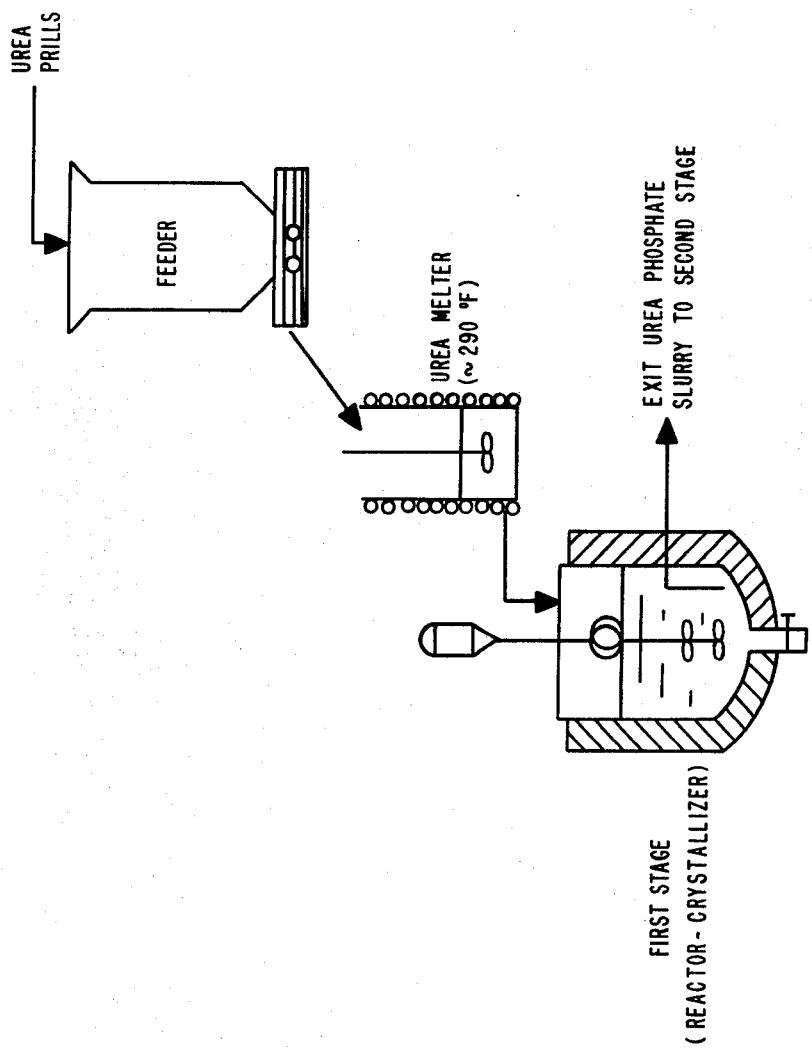
FIG. 3 is a drawing illustrating bench-scale addition of urea melt to the first stage (reactor-crystallizer).

Referring now more specifically to FIG. 2, there is shown a diagram of the equipment we used on tests of the scale smaller than that of a commercial plant and of a size generally referred to as bench scale. The equipment consisted of a mechanical feeder for metering urea, urea melter (FIG. 3), reactor-crystallizer for the first stage, crystallizer for the second stage, cooling and stirring mechanism for each stage, metering pumps and feed tanks. The reactor-crystallizer and crystallizer were of the mixed-bed type. The second stage was equipped with a meter for measuring pH. A batch-type centrifuge (basket 11 inches in diameter by 3.6 inches deep) was used for separating product crystals and mother liquor. A surge and settling tank plus a batch-type centrifuge were used for clarifying the recycle mother liquor. As may be seen in FIG. 2, urea prills (unconditioned, 46 percent N) are fed through a feeder to the first-stage reactor-crystallizer. Simultaneously, wet-process acid (54 percent $P_2O_5$) and recycle mother liquor, to which an acidifying agent was added batchwise prior to a test, are metered to the first stage. When urea melt instead of urea prills was used, the prills were fed to a melter, as illustrated in FIG. 3, and then to the first stage. The urea melt (about 99 percent urea) simulated urea direct from the concentrator of a urea production plant. The melter was maintained at about 290° F., which is about 20 degrees higher than the melting point of urea. The process operated satisfactorily with urea fed as hot melt, but some decomposition of urea occurred in the melter. This condition would not be present in a full-scale production plant. Again referring to FIG. 2, the first stage is cooled with a water jacket below saturation temperature of the solution, thus some crystallization occurs therein. The first stage was equipped with an "eggbeater" type foam breaker and a turbine-type agitator with slanted vanes. A stirring rate of about 2–5 feet per second, tip speed, was adequate for suspending the crystals. As may be seen, the crystals and mother liquor were discharged to the second stage crystallizer through an overflow tube; the tube was positioned about ¾-inch off the bottom of the first stage. Crystallization is completed in the second stage by cooling to 68° F. Coolant, refrigerated to maintain 68° F. in the second stage, was circulated through an external jacket. The turbine-type agitator was operated at propeller tip speed of about 2–5 feet per second which allowed drawoff of the largest crystals together with some of the medium size and smaller crystals. Excessive stirring rates were not used because they cause abrasion and cleavage of crystals and are detrimental to crystal growth. Product slurry, equivalent to about 8.5 percent of the total volume of the second stage, is withdrawn at regular intervals. The intervals at 2.5, 5, or 10 minutes varied with retention times of 0.5, 1.0, or 2.0 hours, respectively. The urea phosphate crystals are separated from mother liquor in a batch-type centrifuge. Product crystals were saved for chemical analyses after near steady-state conditions were established by allowing sufficient production time for the second stage to be filled and emptied about five times. The size (length) of product crystals was determined by microscopic examination which was adequate for obtaining the average size of the bulk amount of the crystals. A polypropylene screen was used that would allow essentially no crystals to pass through the screening surface as undersize. Screens ranged from 150 to 42 mesh. Rate of addition of urea phosphate slurry to the centrifuge (about 120 cm³/s) was such that the crystals were uniformly distributed on the screen. The method utilized more surface area and prevented blinding of screen openings with carbonaceous material. Again, as may be seen in FIG. 2, part of the mother liquor that is separated from the urea phosphate crystals is used as recycle to the first stage after clarification by settling in a surge tank and centrifuging to remove a high proportion of solid impurities. The remainder of the mother liquor is drawn off as byproduct (9-22-0 grade). The production rate of urea phosphate in our bench-scale equipment ranged from about one to seven pounds per hour and varied with retention time in the second stage and with weight ratio of mother liquor to feed acid.

DESCRIPTION OF THE PREFERRED EMBODIMENT(S)

1 Prior Disclosure of Earlier Related Work

Prior to the instant invention and in our earlier work, we studied the effect of process variables on crystal size and product purity. High recycle rate and long retention time favor product quality; however, each increases size of equipment. A balance must be struck between size of equipment and product quality. Wet-process acids derived from uncalcined Florida phosphate ore and calcined North Carolina ore were tested in the process in our earlier work. The composition of the acids is listed below.

| | Source | |
|---|---|---|
| Composition, % | Florida acid (Uncalcined rock) | North Carolina acid (Calcined rock) |
| $P_2O_5$ | 52.5–54.0 | 52.8–53.6 |
| $Al_2O_3$ | 1.1–1.8 | 0.5–0.6 |
| $Fe_2O_3$ | 1.0–1.6 | 1.1–1.4 |
| MgO | 0.5–0.7 | 0.9–1.0 |
| F | 0.8–1.1 | 0.3–0.5 |
| $SO_4$ | 2.0–4.1 | 2.3–3.6 |
| CaO | Trace–0.5 | Trace |
| C | 0.23–0.34 | <0.01 |
| W.I. solids | 0.7–1.8 | 0.9–1.0 |

The composition of the recycle mother liquors that we used in tests with these Florida and North Carolina acids corresponded to near steady-state conditions and is listed below.

| | Recycle mother liquor made from | |
|---|---|---|
| Composition, % | Florida acid (Uncalcined rock) | North Carolina acid (Calcined rock) |
| Total N[a] | 9.0–9.2 | 9.0–9.3 |
| Urea N | 8.7–8.9 | 8.9–9.2 |
| $P_2O_5$ | 22.1–22.6 | 22.4–22.5 |
| $Al_2O_3$ | 2.2–3.0 | 0.9–1.0 |
| $Fe_2O_3$ | 1.5–2.0 | 1.8–2.0 |
| MgO | 0.9–1.1 | 1.8–2.0 |
| F | 0.9–1.6 | 0.4–0.6 |
| $SO_4$ | 4.0–7.5 | 4.0–7.1 |

[a]Total N includes urea N, ammonia N (0.1 to 0.2 percent), and biuret N (0.05 to 0.1 percent) with urea fed to first-stage reactor-crystallizer a prills.

The weight ratio of the average impurity level of mother liquor:acid in the mother liquors made from the Florida and North Carolina acids, supra, was in the range of 3.3 to 3.8. Impurity level was calculated by comparing impurity: $P_2O_5$ ratio in the mother liquor to that in the feed acid, including $SO_4$.

The conditions which we consider to be optimum for cystallization of urea phosphate in our bench-scale equipment are reported in TVA Bulletin Y-136 ("New Developments in Fertilizer Technology," 12th Demonstration, National Fertilizer Development Center, Muscle Shoals, Ala., 17–20, Oct. 18–19.

| First-stage reactor-crystallizer | |
|---|---|
| Mole ratio of urea to $H_3PO_4$ in feed and mother liquor | 1.0 |
| Weight ratio of recycle mother liquor to feed acid | 2.0–3.0 |
| Retention time, h | 1.0–2.0 |
| Operating temperature (temperatures are 16° to 17° F. below the saturation temperature of the feed solution) | |

| -continued | |
|---|---|
| With recycle ratio of 2.0 | 90° F. |
| With recycle ratio of 3.0 | 85° F. |
| Agitator tip speed | 3-4 ft/s |
| Second-stage crystallizer | |
| Retention time | 1.0-2.0 h |
| Temperature | 68° F. |
| Agitator tip speed | 3-4 ft/s |
| Centrifuge (batch-type; basket, 11 in diam by 3.6 in deep for separating crystals and mother liquor) | |
| r/min | 2,400-3,000 |
| G | 900-1,400 |
| Rate of addition of urea phosphate slurry (crystals uniformly distributed on screen) | 120 cm³/s |
| Batch volume | 600 cm³ |
| Batch time | 10 s |
| Filter screen | 60-48 mesh |
| Product cake thickness | 0.2 in. |
| Moisture content of crystals | 1%-2% by wt. |

The urea phosphate crystals, after air drying at about 100° F. contain about 17.3 to 17.5 percent nitrogen and 44.0 to 44.5 percent $P_2O_5$, compared with the theoretical composition of 17.7 and 44.9 percent, respectively. About 80 percent of the acid $P_2O_5$ and urea is recovered as relatively pure urea phosphate. These crystals contain only about 10 percent to 15 percent of the iron, aluminum, magnesium, and fluorine from the feed acid. The average size (length) of the urea phosphate crystals ranges from 610 to 850 microns. The byproduct mother liquor contains about 20 percent of the acid $P_2O_5$ and 85 to 90 percent of the impurities.

2. Work Relating Directly to the Instant Invention

Figure 4:
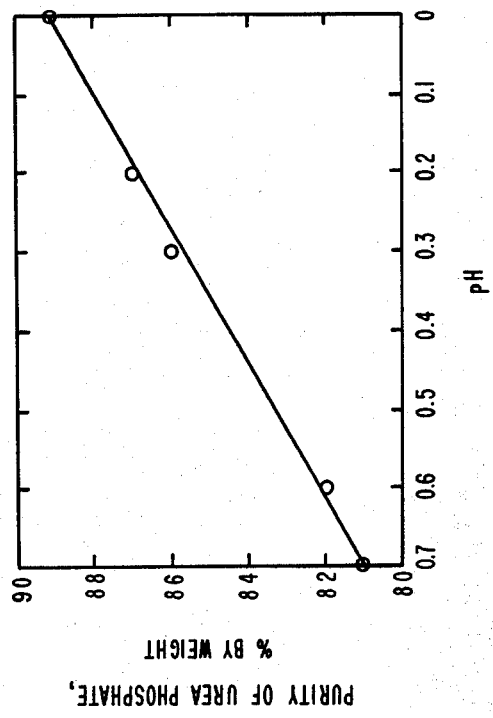
FIG. 4 is a curve showing purity of urea phosphate versus pH in the process for tests of addition of sulfuric acid to mother liquor.

Referring now more specifically to FIG. 4, there is shown a curve showing purity of urea phosphate versus pH in the process for tests we made of addition of sulfuric acid to mother liquor. This curve shows the very significant increases in urea phosphate purity effected by decreasing pH in the process by addition of an acidifying agent. The urea phosphate was produced in batch-type tests, for convenience, and the mother liquor was made from merchant-grade Florida acid derived from uncalcined phosphate ore. A plot of product purity versus pH in the process shows a linear relationship, as represented by the equation $$\text{wt \% product purity} = -11.73 \, (\text{pH}) + 89.23$$

which has a correlation coefficient of 0.99.

EXAMPLES

In order that those skilled in the art may understand how the present invention can be practiced and more fully and definitely understood, the following examples that we have used for production of urea phosphate prepared according to our invention are given by way of illustration and not by way of limitation.

EXAMPLE I

Unconditioned urea prills (46 percent N) were fed to the first stage (FIG. 2) through a feeder. Effective volume of the first stage was 2210 cm³. Simultaneously, merchant-grade wet-process acid derived from calcined western ore and clarified recycle mother liquor to which sulfuric acid (95.8 percent $H_2SO_4$) was added prior to the test were metered to the first stage. The clarified mother liquor before $H_2SO_4$ addition was of low-solids content and contained predominantly the fine grained crystals of the iron phosphate-urea salt. The first stage was maintained at 90° F. (about 17° F. below saturation temperature of the solution) by cooling with a water jacket. Stirring rate in the first stage was 4 feet per second (propeller tip speed). The feed rate of urea, wet-process acid, and mother liquor was 7.0, 16.0, and 32.1 grams per minute, respectively.

The feed acid contained all of the solid impurities present in the original acid. The acid contained 51.4 percent $P_2O_5$, 1.5 percent $Al_2O_3$, 1.0 percent $Fe_2O_3$, 0.6 percent MgO, 0.9 percent F, 3.1 percent $SO_4$, 0.2 percent CaO, and 0.6 percent water-insoluble solids. The amount of sulfuric acid added (5.37 g of 95.8 percent $H_2SO_4$/100 g mother liquor equivalent to about 103 lb $H_2SO_4$/ton mother liquor) raised the sulfate content of the recycle mother liquor from 5.5 to 10 percent and the specific gravity from 1.44 to 1.47. The mother liquor, prior to $H_2SO_4$ addition, was about 9-22-0 grade and was typical of mother liquor at near steady-state conditions (2.6 percent $Al_2O_3$, 1.5 percent $Fe_2O_3$, 1.1 percent MgO, 1.1 percent F, and 5.5 percent $SO_4$). The pH of the mother liquor was measured with a Leeds and Northrup instrument (Model No. 7413) equipped with a reference electrode and calomel measuring electrode. The pH of the mother liquor in the feed tank was 0.8 at 80° F. prior to addition of sulfuric acid and was 0.3 after adding sulfuric acid. Retention time in first stage and in the second stage was the same, 1.0 hour. The mole ratio of urea to phosphoric acid in the feed was 1.0 and the weight ratio of recycle mother liquor to feed acid was 2.0.

As may be seen in FIG. 2, supra, urea phosphate slurry (22 weight percent product crystals) overflowed from the first stage to the second stage (effective volume, 2210 cm³). Crystallization was completed in the second stage by refrigeration to 68° F.; the slurry in the second stage contained 27 weight percent urea phosphate crystals. Stirring rate in the second stage was 4 feet per second (propeller tip speed). The pH in the urea phosphate slurry in the second stage was 0.3. Product slurry (184 cm³/5 min) was withdrawn from the second stage and the urea phosphate crystals were separated from mother liquor in the batch-type centrifuge operated at 900 G (2400 r/min) for 10 seconds; a polypropylene screen (48 mesh) was used in the centrifuge basket. Samples of product crystals were saved for chemical analyses after about five hours of production time. Product crystals as removed from the centrifuge were about 17-44-0 grade and contained about 2 percent moisture. Fresh mother liquor from the centrifuge was settled in a surge tank and clarified further by centrifuging. About 80 percent of the mother liquor was added to the feed tank as clarified mother liquor for use as recycle. The remaining 20 percent of the mother liquor, which contained most of the impurities originally present in the wet-process acid, was removed from the process as byproduct mother liquor of about 9-22-0 grade. The byproduct mother liquor was suitable for processing into a 16-38-0 grade solid fertilizer or a 15-22-0 grade suspension.

The product crystals were white with a light green tinge and were 650 micrometers in average crystal size. The crystals, air dried at 110° F., contained 17.5 percent nitrogen and 44.2 percent $P_2O_5$ as compared with the theoretical composition of 17.7-44.9-0 for urea phosphate. In impurities, the crystals contained 0.19 percent $Al_2O_3$, 0.16 percent $Fe_2O_3$, 0.06 percent MgO, 0.07 percent F, 0.7 percent $SO_4$, and 0.5 percent $H_2O$. The average purification level of the product (reduction of impurity level calculated by comparing aluminum to $P_2O_5$, iron to $P_2O_5$, magnesium to $P_2O_5$, and fluorine to $P_2O_5$ ratios of the product to those of the feed wet-process acid) was 86 percent. About 80 percent of the acid $P_2O_5$ and urea was recovered as product crystals.

Petrographic examination showed that the product crystals were 99+ percent urea phosphate and contained <1 percent of the iron-aluminum-potassium phosphate salt [$(Fe,Al)_3KH_{14}(PO_4)_8 \cdot 4H_2O$] and chukhrovite ($Ca_4SO_4SiAlF_{13} \cdot 12H_2O$) originally present in the feed wet-process acid. No iron phosphate-urea salt was present. Sulfuric acid solubilized the limited quantity of iron phosphate-urea salt initially present in the recycle mother liquor and prevented further precipitation during the test.

Petrographic examination showed no evidence of the presence of urea sulfate.

Other tests of the crystallization process involving addition of acidifying agents to mother liquor are shown in tables I, II, III, IV and V, infra. The crystallization tests were made in the bench-scale continuous equipment shown in FIG. 2, supra, and for convenience, in batch-type laboratory-scale equipment.

These data (Table I, infra) were obtained in five continuous bench-scale tests (No. 1-5) that we made to study addition of sulfuric acid to clarified recycle mother liquor to improve purity of the crystalline urea phosphate produced from urea and merchant-grade wet-process acid derived from calcined western phosphate ore in the continuous two-stage crystallization process. Three of the five tests were made without sulfuric acid addition to the recycle mother liquor—two with retention time of 1.0 hour in each stage and one with increased retention time (2.0 vs 1.0 h) in the second stage to further test the effect of retention time on size and purity of the product crystals. Retention time was 1.0 hour in each stage for the two tests that were made with sulfuric acid added to the recycle mother liquor. The amount of sulfuric acid added (about 103 lb $H_2SO_4$/ton mother liquor) increased the sulfate content of the mother liquor from 5.5 to 10 percent. We have found in our experimental work using Florida black acid (54 percent $P_2O_5$) that recovery at 68° F. of acid $P_2O_5$ and urea as solid urea phosphate varied only 1 to 2 percentage points when the sulfate content of the recycle mother liquor was varied over the range of 5.5 to 12.5 percent (about 4 to 8 percent $SO_4$ in process). Although this variation in sulfate content appeared to have no appreciable effect on product recovery, it did result in very significant increases in product purity. The composition of the feed acid from calcined western ore and that of the recycle mother liquor are given in Example I, supra. Operating conditions and results of the tests are shown in Table I below.

TABLE I

Two-Stage Crystallization Process for Continuous Production of Urea Phosphate from Urea and Wet-Process Acid[a] Derived from Calcined Western Phosphate Ore

| Test No. | 1 | 2 | 3 | 4 | 5 |
|---|---|---|---|---|---|
| Recycle mother liquor[b] (clarified) | | | | | |
| Conc $H_2SO_4$ added[c] | No | No | No | Yes | Yes |
| $SO_4$ level, % by wt | 5.5 | 5.5 | 5.5 | 10 | 10 |
| pH | 0.8 | 0.8 | 0.8 | 0.3 | 0.3 |
| $SO_4$ level in process, % by wt | 4.1 | 4.1 | 4.1 | 6.8 | 6.8 |
| First stage (reactor-crystallizer) | | | | | |
| Mole ratio urea:$H_3PO_4$ in feed | 1.0 | 1.0 | 1.0 | 1.0 | 1.0 |
| and mother liquor | | | | | |
| Wt ratio recycle mother liquor to feed acid | 2.0 | 2.0 | 2.0 | 2.0 | 2.0 |
| Operating temperature, °F. | 90 | 90 | 90 | 90 | 90 |
| Feed, g/min | | | | | |
| Urea (unconditioned prills, 46% N) | 5.5 | 5.5 | 5.5 | 5.6 | 7.0 |
| Wet-process acid | 12.7 | 12.7 | 12.7 | 12.9 | 16.0 |
| Mother liquor | 25.4 | 25.4 | 25.5 | 25.7 | 32.1 |
| Volume, $cm^3$ | 1773 | 1773 | 1773 | 1773 | 2210 |
| Second stage (crystallizer) | | | | | |
| Operating temperature, °F. | 68 | 68 | 68 | 68 | 68 |
| pH in urea phosphate slurry | 0.7 | 0.7 | 0.7 | 0.3 | 0.3 |
| Volume, $cm^3$ | 1773 | 1773 | 3546 | 1773 | 2210 |
| Retention time, h | | | | | |
| First stage | 1.0 | 1.0 | 1.0 | 1.0 | 1.0 |
| Second stage | 1.0 | 1.0 | 2.0 | 1.0 | 1.0 |
| Batch-type centrifuge for separating mother liquor and crystals | | | | | |
| R/min | 2400 | 2400 | 2400 | 2400 | 2400 |
| G | 900 | 900 | 900 | 900 | 900 |
| Batch time, s | 10 | 10 | 10 | 10 | 10 |
| Filter screen, mesh | 48 | 48 | 48 | 48 | 48 |
| Product cake thickness, in. | 0.2 | 0.2 | 0.2 | 0.2 | 0.2 |
| Product urea phosphate[d] from second stage | | | | | |
| Percent by wt | | | | | |
| N | 17.2 | 17.3 | 17.2 | 17.5 | 17.5 |
| $P_2O_5$ | 44.0 | 44.0 | 43.9 | 44.1 | 44.2 |
| $Al_2O_3$ | 0.30 | 0.33 | 0.29 | 0.21 | 0.19 |
| $Fe_2O_3$ | 0.22 | 0.24 | 0.22 | 0.17 | 0.16 |
| MgO | 0.11 | 0.13 | 0.10 | 0.07 | 0.06 |
| F | 0.12 | 0.13 | 0.11 | 0.08 | 0.07 |
| $SO_4$ | 0.6 | 0.7 | 0.6 | 0.8 | 0.7 |
| $H_2O$ | 0.7 | 0.7 | 0.6 | 0.5 | 0.5 |
| Avg crystal size, micrometers | 640 | 610 | 705 | 640 | 650 |
| Avg reduction of impurities (Al, Fe, Mg, F),[e] % | 78 | 76 | 79 | 85 | 86 |

[a] Composition of wet-process acid given in Example I.
[b] Compositon of recycle mother liquor given in Example I.
[c] Addition of acid (95.8% $H_2SO_4$) equivalent ot about 103 lb $H_2SO_4$/ton mother liquor.
[d] Product crystals were air dried at 110° F.; products were white in color with a light green tinge.
[e] Calculated by comparing impurity to $P_2O_5$ ratio in the product with that in the feed acid.

EXAMPLE II

See Table I, supra

In tests numbers 1 and 2 (no sulfuric acid added to the recycle mother liquor), pH of the mother liquor was 0.8; pH in the urea phosphate slurry in the second stage (68° F.) was about the same, 0.7. Retention time in these tests was 1.0 hour in each stage. Product purity (average reduction of impurities calculated by comparing impurity to $P_2O_5$ ratio in the product with that in the feed acid) was 76–78 percent and average crystal size was 610–640 micrometers. The product crystals, air dried at 110° F., contained 17.2 to 17.3 percent nitrogen and 44.0 percent $P_2O_5$ which is close to the theoretical composition of urea phosphate (17.7-44.9-0). The crystals were white in color with a light green tinge.

EXAMPLE III

See Table I, supra

In test number 3 (no sulfuric acid added to recycle mother liquor), increasing the retention time from 1.0 to 2.0 in the second stage resulted in larger crystal size (705 vs 610 micrometers in test number 2); however, product purity (79 percent) was about the same as in tests 1 and 2. The product crystals, air dried at 110° F., contained 17.2 percent nitrogen, 43.9 percent $P_2O_5$, and were white in color with a light green tinge.

EXAMPLE IV

See Table I, supra

Sulfuric acid was added to the recycle mother liquor in tests numbers 4 and 5. Addition of the sulfuric acid increased the sulfate content of the mother liquor from 5.5 to 10 percent and decreased pH of the liquor from 0.8 to 0.3. The pH in the urea phosphate slurry in the second stage was 0.3. Decreasing pH by addition of sulfuric acid resulted in increased product purity compared with similar tests (Nos. 1 and 2) without sulfuric acid addition (85-86 percent vs 76-78 percent). Average crystal size was about 650 micrometers, about the same as in tests without sulfuric acid addition. The product crystals, air dried at 110° F., contained 17.5 percent nitrogen, 44.1-44.2 percent $P_2O_5$, and were white in color with a light green tinge.

EXAMPLE V

Petrographic examinations were made of the product crystals from test numbers 1-5 (Table I). Results indicated that the product crystals from tests 1, 2, and 3 (no sulfuric acid added to recycle mother liquor; product purity was 76-79 percent) contained 95+ percent urea phosphate, <2 percent of the iron phosphate urea salt [$FeH_3(PO_4)_2 \cdot 2CO(NH_2)_2$], and <1 percent of the iron-aluminum-potassium phosphate solid and chukhrovite originally present in the feed wet-process acid. Similar petrographic examinations showed that product crystals from tests 4 and 5 (sulfuric acid added to recycle mother liquor; product purity was 85-86 percent) were 99+ percent urea phosphate and <1 percent each of the iron-aluminum-potassium phosphate solid and chukhrovite originally present in the feed wet-process acid. No iron phosphate-urea salt was present. Sulfuric acid solubilized the limited quantity of iron phosphate-urea salt initially present in the recycle mother liquor and prevented further precipitation.

EXAMPLE VI

See Table I, supra

The urea phosphate products from test numbers 1-5 were processed into urea-ammonium polyphosphate liquid fertilizers by batch-type pyrolysis of the crystals at 260° to 275° F. followed by addition of water and ammonia gas. Data in the following tabulation show that very significant increases in storage life of the liquids were obtained with increases in product purity by addition of sulfuric acid in the process.

| Urea phosphate products (Table I) | | Storage time at 80° F. (months) of liquid fertilizer (15-28-0 grade, 50% of $P_2O_5$ as polyphosphate) Very good condition[a] |
|---|---|---|
| Test No. | $H_2SO_4$ added in process | Product purity, % |
| 1 | No | 78 | ¾ |
| 2 | No | 76 | ¾ |
| 3 | No | 79 | ¾-4 |
| 4 | Yes | 85 | 4-6 |
| 5 | Yes | 86 | >12 |

[a]Liquids are considered to store in very good condition when they develop no more than 1% by volume of nonadhering-type crystals (carbonaceous material, ammonium phosphates, urea, and biuret) and a maximum of 0.1% by volume of adhering-type crystals [$MgAl(NH_4)_5-(P_2O_7)_2F_2 \cdot 6H_2O$] - method developed at National Fertilizer Development Center, TVA, Muscle Shoals, Alabama.

Data (Tables II through V, infra) were obtained in batch-type tests of crystallization of urea phosphate with addition of different acidifying agents to mother liquor. The tests were designed to show the effectiveness of varying the proportion of acidifying agent on pH in the process and product purity. Data and results of tests of addition of concentrated sulfuric acid (97.2 percent), concentrated hydrochloric acid (37.4 percent), phosphoric acid (73.2 percent) from merchant-grade acid derived from uncalcined Florida phosphate ore, and concentrated nitric acid (71.0 percent) to mother liquor are given below in Tables II, III, IV, and V, respectively. Merchant-grade acid derived from uncalcined Florida phosphate ore and urea (unconditioned prills, 46.4 percent urea N) were used as feed materials in the tests.

TABLE II

Crystallization of Urea Phosphate from Urea and Wet-Process Acid[a] - Effect of Addition of Sulfuric Acid on pH of Mother Liquor and Purity of Product Crystals

| Test No.[b] | $SO_4$ level, % by wt | | Mother liquor | | Urea phosphate slurry (68° F.) | Product urea phosphate[e] | | |
|---|---|---|---|---|---|---|---|---|
| | In mother liquor[c] | In process[d] | Conc $H_2SO_4$ (97.2%) added, g | pH after $H_2SO_4$ addition | pH of mother liquor separated from cake by centrifugation | % by wt | | Average reduction of impurities (Al, Fe, Mg, F), %[f] |
| | | | | | | N | $P_2O_5$ | |
| 6 | 4 | 3.3 | 0 | 0.7 | 0.6 | 17.5 | 44.5 | 82 |
| 7 | 7.5 | 5.4 | 10.7 | 0.5 | 0.3 | 17.5 | 44.4 | 86 |
| 8 | 10 | 6.9 | 18.8 | 0.3 | 0.2 | 17.4 | 44.4 | 87 |
| 9 | 12.5 | 8.5 | 27.5 | 0.2 | 0[g] | 17.4 | 44.4 | 89 |

[a]Merchant-grade acid (53.0% $P_2O_5$) derived from uncalcined Florida phosphate ore.
[b]Charge: 60.4 g unconditioned urea prills (46.4% urea N); 133.95 g of merchant-grade Florida black acid; 267.9 g mother liquor; 0-27.5 g concentrated (97.2%) $H_2SO_4$ added to mother liquor. Each test made with mole ratio urea:$H_3PO_4$ = 1.0 and wt ratio mother liquor to feed acid, 2.0.
[c]Calculated by comparing $SO_4$ content in 267.9 g mother liquor (4% $SO_4$) plus amount in added $H_2SO_4$ with total weight of solution.
[d]Calculated by comparing $SO_4$ content in charge (footnote [b]) with total weight.
[e]Product crystals air dried at 110° F. Crystal size was in range of about 350 to 600 micrometers.
[f]Calculated by comparing impurity to $P_2O_5$ ratio in the product with that in the feed acid.
[g]Estimated pH 0.01.

TABLE III

Crystallization of Urea Phosphate from Urea and Wet-Process Acid[a] -
Effect of Addition of Hydrochloric Acid on pH of Mother Liquor and Purity of Product Crystals

| Test No.[b] | HCl level in mother liquor, % by weight | Mother liquor Conc HCl (37.4%) added, g | Urea phosphate slurry (68° F.) pH of mother liquor separated from cake by centrifugation | Product urea phosphate[c] % by wt N | P$_2$O$_5$ | Average reduction of impurities (Al, Fe, Mg, F), %[d] |
|---|---|---|---|---|---|---|
| 10 | 0 | 0 | 0.6 | 17.4 | 44.4 | 79 |
| 11 | 1 | 7.4 | 0.5 | 17.5 | 44.3 | 79 |
| 12 | 4 | 32.1 | 0[e] | 17.6 | 44.6 | 87 |
| 13 | 7.5 | 67.2 | 0[e] | 17.5 | 44.5 | 88 |
| 14 | 10 | 97.8 | 0[e] | 17.5 | 44.4 | 88 |

[a]Merchant-grade acid (53.0% P$_2$O$_5$) derived from uncalcined Florida phosphate ore.
[b]Charge: 60.4 g unconditoned urea prills (46.4% urea N); 133.95 g of merchant-grade Florida black acid; 267.9 g mother liquor; 0-97.8 g concentrated (37.4%) HCl added to mother liquor. Each test made with mole ratio urea:H$_3$PO$_4$ = 1.0 and weight ratio mother liquor to feed acid, 2.0.
[c]Product crystals air dried at 110° F. Crystal size was in range of 300 to 385 micrometers.
[d]Calculated by comparing impurity to P$_2$O$_5$ ratio in product with that in feed acid.
[e]Estimated pH 0.01.

TABLE IV

Crystallization of Urea Phosphate from Urea and Wet-Process Acid[a] -
Effect of Addition of Phosphoric Acid on pH of Mother Liquor and Purity of Product Crystals

| Test No.[b] | Mother liquor Merchant-grade Florida black acid (73.2% H$_3$PO$_4$) added, g | Increase in H$_3$PO$_4$ level, % by wt | Mole ratio urea:H$_3$PO$_4$ | Urea phosphate slurry (68° F.) pH of mother liquor separated from cake by centrifugation | Product urea phosphate[c] % by wt N | P$_2$O$_5$ | Average reduction of impurities (Al, Fe, Mg, F), %[d] |
|---|---|---|---|---|---|---|---|
| 15 | 0 | 0 | 1.00 | 0.5 | 17.4 | 44.4 | 79 |
| 16 | 15.5 | 4 | 0.90 | 0.4 | 17.4 | 44.5 | 80 |
| 17 | 30.6 | 7.5 | 0.81 | 0.4 | 17.4 | 44.5 | 81 |
| 18 | 42.4 | 10 | 0.76 | 0.3 | 17.4 | 44.3 | 83 |
| 19 | 55.2 | 12.5 | 0.71 | 0.3 | 17.4 | 44.6 | 84 |

[a]Merchant-grade acid (53.0% P$_2$O$_5$) derived from uncalcined Florida phosphate ore.
[b]Charge: 60.4 g unconditioned urea prills (46.4% urea N); 133.95 g of merchant-grade Florida black acid; 267.9 g mother liquor; 0-55.2 g merchant-grade Florida black acid added to mother liquor. Each test made with mole ratio urea:H$_3$PO$_4$ in feed = 1.0 and weight ratio mother liquor to feed acid, 2.0.
[c]Product crystals air dried at 110° F. Crystal size was in range of 475 to 530 micrometers.
[d]Calculated by comparing impurity to P$_2$O$_5$ ratio in the product with that in the feed acid.

The batch-type equipment consisted of a 600-cubic-centimeter pyrex beaker (used as a reactor-crystallizer), a variable speed stirrer, a hot plate, a constant temperature bath operated at 68° F., a centrifuge (IEC, Model 2K), and a Leeds and Northrup pH meter (Model No. 7413) equipped with a reference electrode and a calomel measuring electrode. The basket (8 in diameter by 3 in deep) in the centrifuge was equipped with a 100-mesh polypropylene cloth for separating mother liquor from product crystals.

A mole ratio of urea to phosphoric acid of 1.0 in the feed and a weight ratio of mother liquor to feed acid of 2.0 were used in the tests. The acidifying agent was added batchwise to the mother liquor prior to a test. Sulfuric acid was added in proportions to vary the sulfate level in the mother liquor from 4 to 12.5 percent; concentrated hydrochloric acid and nitric acid were added in proportions to give levels of either HCl or HNO$_3$ of 0 to 10 percent by weight in the mother liquor. Phosphoric acid was added as the merchant-grade Florida feed acid in proportions to increase the H$_3$PO$_4$ level of the mother liquor from 0 to 12.5 percent by weight.

The merchant-grade acid derived from uncalcined Florida phosphate ore contained 53.0 percent P$_2$O$_5$, 1.8 percent Al$_2$O$_3$, 1.3 percent Fe$_2$O$_3$, 0.6 percent MgO, 0.9 percent F, and 3.4 percent SO$_4$. The average impurity level of the mother liquor used in these tests was lower than that of mother liquors at near steady-stage conditions (2.5 vs about 3.3-3.8). Prior to addition of a test acid (H$_2$SO$_4$, HCl, H$_3$PO$_4$ or HNO$_3$) the mother liquor contained 8.6 percent urea N, 22.1 percent P$_2$O$_5$ (mole ratio urea:H$_3$PO$_4$, 1.0), 1.6 percent Al$_2$O$_3$, 1.4 percent Fe$_2$O$_3$, 0.8 percent MgO, 0.7 percent F, and 4 percent SO$_4$. The mother liquor was of relatively low-solids content and contained a higher proportion of the fine grained crystals of the iron phosphate-urea salt than normally present in clarified recycle mother liquor. After addition of a test acid to the mother liquor, the mixture was allowed to equilibrate overnight before a urea phosphate crystallization test was made.

The following procedure was used in the batch-type tests. Urea (60.4 g), wet-process acid (133.95 g) and mother liquor (267.9 g), with the acidifying agent added or omitted, were mixed in a 600-cubic-centimeter pyrex beaker and heated to about 120° F. to ensure dissolution of the prilled urea. The solution then was stirred (with addition of 0.5 g of seed crystals) and cooled slowly to 68° F. The resulting urea phosphate slurry was maintained at 68° F. for 2 hours to ensure maximum crystallization under test conditions. The slurry was centrifuged at 900 G for 10 seconds and the pH of the mother liquor separated from the crystals was measured. Product cake was air dried at 110° F. and the dried crystals were submitted for chemical analysis and petrographic examination.

EXAMPLE VII

See Table II, supra

In test 6 (made with no added sulfuric acid) the sulfate content of the mother liquor was 4 percent, pH in the urea phosphate slurry (process) was 0.6 and product purity was 82 percent. Addition of sulfuric acid to increase sulfate level in the mother liquor over the range of from 4 to 12.5 percent caused progressive decreases in pH from 0.6 to 0 and increases in product purity from 82 to 89 percent. The products air dried at 110° F. contained 17.4 to 17.5 percent nitrogen and 44.4 to 44.5 percent $P_2O_5$ which is close to the theoretical composition of urea phosphate (17.7-44.9-0).

Petrographic examinations were made of the product crystals from tests 6-9, Table II supra. Results indicated that product crystals from test 6 (no sulfuric acid added to mother liquor, 4 percent $SO_4$; product purity was 82 percent) contained 95+ percent urea phosphate, <2 percent of the iron phosphate-urea salt and <1 percent chukhrovite originally present in the feed wet-process acid. Similar petrographic examinations showed that product crystals from tests 7 through 9 (sulfuric acid added to give 7.5, 10, and 12.5 percent sulfate level in mother liquor; product purity was 86-89 percent) contained 95+ percent urea phosphate, a lower proportion of the iron phosphate-urea salt (<1 percent vs <2 percent) and <1 percent chukhrovite.

EXAMPLE VIII

See Table III, supra

With no hydrochloric acid added to the mother liquor (test 10), pH in the process was 0.6 and product purity was 79 percent. Increasing the HCl level of the mother liquor to 1 percent decreased pH in the process only from 0.6 to 0.5 and product purity remained the same, 79 percent. Increasing the HCl level from 1 to 4 percent decreased pH in the process from 0.5 to 0 and increased product purity significantly (87 vs 79 percent). Further addition of hydrochloric acid to increase its level in the mother liquor over the range of from 4 to 10 percent resulted in no appreciable increase in product purity. The products, air dried at 110° F., contained 17.4 to 17.6 percent nitrogen and 44.3 to 44.6 percent $P_2O_5$, which is close to the theoretical composition of urea phosphate (17.7-44.9-0).

Petrographic examinations were made of the product crystals from tests 10-14; see table III, supra. Results indicated that product crystals from tests 10 and 11 (0 and 1 percent HCl level, respectively, in mother liquor; product purity was 79 percent) contained 95+ percent urea phosphate, <3 percent of the iron phosphate-urea salt and <1 percent chukhrovite originally present in the feed wet-process acid. It is noted that the purification level of the blank (no HCl added) is lower than shown in Table II, supra (79 vs 82 percent product purity) because of continuous precipitation of the contaminating iron phosphate-urea salt in the mother liquor and the time interval of one week between the two series of tests. Product crystals from test 12 (HCl added to give a 4 percent level in mother liquor; product purity was 87 percent) contained 95+ percent urea phosphate, <2 percent iron phosphate-urea salt, and <1 percent chukhrovite. Similar petrographic examination of product crystals from tests 13 and 14 (7.5 and 10 percent HCl level, respectively, in mother liquor; product purity was 88 percent) contained 95+ percent urea phosphate, <1 percent of the iron phosphate-urea salt and <1 percent chukhrovite. Thus, it can be seen that hydrochloric acid was an effective solvent for the iron phosphate-urea salt.

EXAMPLE IX

See Table IV, supra

Increasing the phosphoric acid level of the mother liquor over the range of 0 to 12.5 percent by additions of merchant-grade Florida black acid caused decreases in pH in the process from 0.5 to 0.3 and progressive increases in product purity from 79 to 84 percent. The products, air dried at 110° F., contained 17.4 percent nitrogen and 44.3 to 44.6 percent $P_2O_5$, which is close to the theoretical composition of urea phosphate (17.7-44.9-0).

Petrographic examinations indicated that product crystals from tests 15 through 19 (table IV) contained 95+ percent urea phosphate, <3 percent of the iron phosphate-urea salt and <1 percent chukhrovite originally present in the feed wet-process acid. No appreciable differences in amounts of the iron phosphate-urea salt with different levels of phosphoric acid addition were detected. However, the purification level (79-84 percent) of the urea phosphate crystals indicated that phosphoric acid decreased pH and increased product purity; thus, it had some effectiveness in solubilizing the iron phosphate-urea salt.

EXAMPLE X

Addition of nitric acid to mother liquor was not an effective method of increasing purity of the urea phosphate crystals because of precipitation of fine grained urea nitrate. The data indicated that increasing the nitric acid level in the mother liquor over the range of 0 to 10 percent decreased pH in the process from 0.5 to 0, but increased $NO_3$-N content in the product crystals from nil to 2.9 percent and, unlike $H_2SO_4$, HCl, and $H_3PO_4$, decreased product purity from 78 to 47 percent.

Petrographic results were in good agreement with chemical analysis in showing a corresponding increase in urea nitrate crystals in the urea phosphate product with increasing nitric acid concentration. The formation of extremely fine grained urea nitrate crystals (<10 micrometers) caused occlusion of urea phosphate mother liquor on the surface of the urea nitrate crystals as well as the urea phosphate product crystals, which resulted in poor separation in the centrifuge of mother liquor from product crystals and decreased product purity.

The formation of urea-sulfuric acid and urea-hydrochloric acid did not occur when these acids were added to the urea phosphate system. Therefore, these acids ($H_2SO_4$, HCl, and $H_3PO_4$) did not produce any fine grained urea adducts besides the desired urea phosphate and consequently increased the solubility of the contaminating iron phosphate-urea salt $[FeH_3(PO_4)_2 \cdot 2CO(NH_2)_2]$ and purity of the urea phosphate crystals. The results are illustrated in Table V below.

TABLE V

Crystallization of Urea Phosphate from Urea and Wet-Process Acid[a] - Effect of Addition of Nitric Acid on pH of Mother Liquor and Purity of Product Crystals

| Test No.[b] | Mother liquor HNO₃ level, % by wt | Mother liquor Conc HNO₃ (71.0%) added, g | Urea phosphate slurry (68° F.) pH of mother liquor separated from cake by centrifugation | Product urea phosphate[c] Total N | Product urea phosphate[c] % by wt NO₃—N | Product urea phosphate[c] % by wt P₂O₅ | Average reduction of impurities (Al, Fe, Mg, F), %[d] |
|---|---|---|---|---|---|---|---|
| 20 | 0 | 0 | 0.5 | 17.4 | Nil | 44.1 | 78 |
| 21 | 1 | 3.8 | 0.5 | 17.4 | Nil | 44.0 | 78 |
| 22 | 4 | 16.0 | 0.1 | 17.4 | 0.1 | 43.8 | 75 |
| 23 | 7.5 | 31.6 | 0.1 | 18.5 | 1.9 | 37.1 | 61 |
| 24 | 10 | 43.9 | 0[e] | 19.5 | 2.9 | 33.0 | 47 |

[a]Merchant-grade acid (53.0% P₂O₅) derived from Florida uncalcined phosphate ore.
[b]Charge: 60.4 g unconditioned urea prills (46.4% urea N); 133.95 g merchant-grade Florida black acid; 267.9 g mother liquor; 0–43.9 g concentrated (71.0%) HNO₃ added to mother liquor. Each test made with mole ratio urea:H₃PO₄ = 1.0 and weight ratio mother liquor to feed acid, 2.0.
[c]Product crystals air dried at 110° F. Crystal size was in range of 375–550 micrometers.
[d]Calculated by comparing impurity to P₂O₅ ratio in product with that in feed acid.
[e]Estimated pH 0.01.

EXAMPLE XI

Storage of Mother Liquor

Storage tests were made to show the effectiveness of addition of the different acidifying agents, supra, on prolonging the useful storage life of clarified-recycle mother liquor. The mother liquor, which was made from merchant-grade Florida black acid, contained about 7 percent SO₄ and was typical of clarified recycle mother liquor at near steady-state conditions.

Data from the tests indicated that sulfuric acid and hydrochloric acid were very satisfactory solvents for the iron phosphate-urea salt. Mother liquor to which sulfuric acid was added to increase sulfate level from 7 to 11 percent by weight remained in very good condition (<0.1 percent by volume of settled solids) during eight weeks quiescent storage at 80° F. Similar results were obtained with a 4 percent level of hydrochloric acid added in the mother liquor. With no acidifying agent added, the mother liquor contained about 13 percent by volume of settled solids after eight weeks of similar storage. Phosphoric acid was less effective than either hydrochloric acid or sulfuric acid. Nitric acid was unsatisfactory because of precipitation of urea nitrate.

INVENTION PARAMETERS

After sifting and winnowing through data presented above as well as other data available to us, we have determined that the operating limits as well as the preferred conditions for carrying out the instant invention related to use of acidifying agents in the production of urea phosphate are summarized below:

| Acidifying agent added to mother liquor | Limits | Preferred |
|---|---|---|
| Sulfuric acid | | |
| Increase in SO₄ level of mother liquor, % by wt. | >2 and <10 | 4–6 |
| pH in process | <1 and ≧0.01 | 0.3–0.01 |
| Hydrochloric acid | | |
| Level in mother liquor, % by wt | >1 and <8 | 3–4 |
| pH in process | <1 and ≧0.01 | 0.2–0.01 |
| Phosphoric acid | | |
| Increase in H₃PO₄ level of mother liquor, % by wt | >4 and <13 | 10–12 |
| pH in process | <1 and ≧0.3 | 0.4–0.3 |

While we have shown and described particular embodiments of our invention modifications and variations thereof will occur to those skilled in the art. We wish it to be understood therefore that the appended claims are intended to cover such modifications and variations which are within the true scope and spirit of our invention.

What we claim as new and desire to secure by Letters Patent of the United States is:

1. In an improved process for the production of crystalline urea phosphate from wet-process phosphoric acid and urea comprising:

(1) introducing wet-process phosphoric acid and urea into first-stage crystallizing means wherein said wet-process phosphoric acid, containing substantially all of the congeneric impurities relating thereto, is reacted with said urea to produce a slurry of urea phosphate wherefrom at least a portion of said urea phosphate slurry is removed to cooling means and subsequently returned to said first-stage crystallizing means whereby said urea phosphate slurry therein is cooled to at least the saturation temperature of said slurry;

(2) removing at least a portion of said resulting cooled urea phosphate slurry from said first-stage crystallizing means and introducing same into second-stage crystallizing means wherefrom at least a portion thereof is removed to cooling means and subsequently returned to said second-stage crystallizing means to effect the cooling of said urea phosphate slurry therein to a temperature ranging from about 30° F. to about 50° F. below the saturation temperature thereof to effect further and significantly more pronounced crystallization of said urea phosphate therein;

(3) removing at least a portion of the resulting crystallized urea phosphate and slurry from said second-stage crystallizing means to separating means wherefrom a substantial portion of the urea phosphate crystals therein are removed as product and wherefrom the mother liquor comprising urea phosphate solution, urea phosphate crystals, and other precipitated solids is removed to mother liquor surging, settling, and separating means; and (4) removing at least a portion of the treated mother liquor from said mother liquor surging, settling, and separating means, and introducing same as recycle to said first-stage crystallizing means; the improvement in combination therewith for substantially (a) increasing the solubility of at least one of the co-precipitating contaminating materials in said mother liquor, said co-precipitating contaminating material comprising the water insoluble iron phosphate-urea salt [FeH$_3$(PO$_4$)$_2$·2CO(NH$_2$)$_2$]; (b) significantly improving the purity of the crystalline urea phosphate product; and (c) substantially improving the useful storage life characteristics of said recycle mother liquor, which improved process comprises the additional step of adding to at least a portion of the recycled mother liquor removed from said mother liquor surging, settling, and separating means and introduced to said first-stage crystallizing means an acidulating agent selected from the group of mineral acids comprising sulfuric, hydrochloric, phosphoric, and mixtures thereof, in predetermined quantities sufficient to reduce the pH of said mother liquor so removed from said surging, settling, and separating means from the range of about 0.6 to greater than about 1 down to the range of about 0.4 to about 0.01, said improved process characterized by the fact that the normal presence of upwards of about 2 percent by weight of the co-precipitated contaminating iron phosphate-urea salt [FeH$_3$(PO$_4$)$_2$·2CO(NH$_2$)$_2$] in the product crystalline urea phosphate is substantially eliminated therefrom and the average reduction of impurities in the product crystalline urea phosphate is increased from about 8 to about 17 percent.

2. The process of claim 1 wherein said acidulating agent is sulfuric acid and the predetermined quantities of same added thereto is sufficient to reduce the pH of said mother liquor down to the range of about 0.3 to about 0.01.

3. The process of claim 1 wherein said acidulating agent is hydrochloric acid and the predetermined quantities of same added thereto is sufficient to reduce the pH of said mother liquor down to the range of about 0.2 to about 0.01.

4. The process of claim 1 wherein said acidulating agent is phosphoric acid and the predetermined quantities of same added thereto is sufficient to reduce the pH of said mother liquor down to the range of about 0.4 to about 0.3.

5. The process of claim 2 wherein the average reduction of impurities in the product crystalline urea phosphate ranges upwards to about 89 percent calculated by comparing the impurity weight percent:weight percent P$_2$O$_5$ in said product with the impurity weight percent:weight percent P$_2$O$_5$ in said wet-process phosphoric acid introduced into said first-stage crystallizing means. means.

6. The process of claim 3 wherein the average reduction of impurities in the product crystalline urea phosphate ranges upwards to about 88 percent calculated by comparing the impurity weight percent:weight percent P$_2$O$_5$ in said product with the impurity weight percent:weight percent P$_2$O$_5$ in said wet-process phosphoric acid introduced into said first-stage crystallizing means.

7. The process of claim 4 wherein the average reduction of impurities in the product crystalline urea phosphate ranges upwards to about 84 percent calculated by comparing the impurity weight percent:weight percent P$_2$O$_5$ in said product with the impurity weight percent:weight percent P$_2$O$_5$ in said wet-process phosphoric acid introduced into said first-stage crystallizing means.

8. The process of claim 2, or 3, or 4, or 5, or 7 wherein said urea introduced into said first-stage crystallizing means is in the form of a melt and at a temperature in the range of about 275° F. to about 285° F.

* * * * *